United States Patent [19]
Cohen et al.

[11] Patent Number: 6,139,827
[45] Date of Patent: Oct. 31, 2000

[54] WEAR COSMETIC COMPOSITION

[75] Inventors: Kenneth Cohen, Thornhill, Canada; Melanie Crim, Scotch Plains; Daniel Ross, Woodbridge, both of N.J.

[73] Assignee: L'Oreal, Paris, France

[21] Appl. No.: 09/001,459

[22] Filed: Dec. 31, 1997

[51] Int. Cl.$^7$ .............................. A61K 7/06; A61K 7/08; A61K 7/00; A61K 31/19; A61K 31/045
[52] U.S. Cl. .................... 424/70.16; 424/70.17; 424/70.22; 424/401; 514/568; 514/729
[58] Field of Search .......................... 424/401, 64, 70.16, 424/70.17, 70.22; 514/568, 729

[56] References Cited

U.S. PATENT DOCUMENTS

| | | |
|---|---|---|
| 3,456,008 | 7/1969 | Stedman . |
| 3,546,008 | 12/1970 | Shields et al. . |
| 3,734,874 | 5/1973 | Kibler et al. . |
| 3,779,993 | 12/1973 | Kibler et al. . |
| 3,784,874 | 1/1974 | Barrett et al. . |
| 3,927,199 | 12/1975 | Micchelli et al. . |
| 4,233,196 | 11/1980 | Sublett . |
| 4,315,910 | 2/1982 | Nowak, Jr. et al. . |
| 4,335,220 | 6/1982 | Coney . |
| 4,340,519 | 7/1982 | Kotera et al. . |
| 4,829,092 | 5/1989 | Nelson et al. . |
| 4,946,932 | 8/1990 | Jenkins . |
| 4,983,377 | 1/1991 | Murphy et al. . |
| 5,143,722 | 9/1992 | Hollenberg et al. . |
| 5,204,090 | 4/1993 | Han . |
| 5,260,052 | 11/1993 | Peters et al. . |
| 5,266,322 | 11/1993 | Myers et al. . |
| 5,288,493 | 2/1994 | Martino et al. . |
| 5,310,508 | 5/1994 | Subramanyam et al. . |
| 5,314,684 | 5/1994 | Horoschak et al. . |
| 5,435,993 | 7/1995 | Hamilton et al. . |
| 5,451,254 | 9/1995 | Andrean et al. . |
| 5,508,024 | 4/1996 | Tranner . |
| 5,519,063 | 5/1996 | Mondet et al. . |
| 5,736,125 | 4/1998 | Morawsky et al. . |

FOREIGN PATENT DOCUMENTS

| | | |
|---|---|---|
| 96/33689 | 10/1996 | WIPO . |

OTHER PUBLICATIONS

Eastman Chemical Company, Eastman AQ 55S and Eastman AQ 38S Polyester Polymers For Cosmetic Applications, Publication CB–28A, Jul. 1994 pp. 1–6.

National Starch and Chemical Company, Personal Care Polymers, Deermacryl LT For Skin Care Formulations, 1994, pp. 1–4.

*Primary Examiner*—Thurman K. Page
*Assistant Examiner*—Alysia Berman
*Attorney, Agent, or Firm*—Oblon, Spivak, McClelland, Maier & Neustadt, P.C.

[57] ABSTRACT

The present invention provides a cosmetic composition, that includes:

(A) a polymer having repeating units resulting from the polymerization of the following monomers:
 (1) an alkyl acrylate and/or methacrylate,
 (2) an N-alkyl acrylamide, and
 (3) an acrylic and methacrylic acid;

(B) a polyester or polyesteramide having repeating units resulting from the polymerization of the following monomers:
 (1) isophthalic acid,
 (2) 5-sulfoisophthalic acid,
 (3) diethylene glycol and 1,4-cyclohexanedimethanol or a mixture of diethylene glycol and 1,4-cyclohexanedimethanol and at least one diamine having two —NRH groups, where R is hydrogen of a $C_1$–$C_4$ alkyl group, and
 (4) optionally, at least one difunctional reactant selected from the group including hydroxycarboxylic acids having one —$C(R)_2$—OH group, aminocarboxylic acids having one —NHR group and aminoalcohols having one —$C(R)_2$—OH group and one —NHR group, where R is as defined above; and an alkoxylated carboxylic acid surfactant having the formula:

$$RCO-(OCH_2CH_2)_n OOCR$$

wherein R is a residue of a polymer of a hydroxy $C_8$–$C_{28}$ acid and n is from 10–60. The composition is particularly useful for film-forming cosmetic applications and improved wear cosmetic foundations.

43 Claims, No Drawings

WEAR COSMETIC COMPOSITION

BACKGROUND OF THE INVENTION

1. Field of the Invention

The present invention is directed to a composition containing (A) an acrylate/acrylamide copolymer and (B) a sulfonated polyester or polyesteramide. The invention composition is useful as, among other things, a cosmetic foundation. Preferred embodiments include an alkoxylated carboxylic acid surfactant and are liquid cosmetics.

2. Discussion of the Background

Cosmetic foundations are used to enhance skin features and mask skin imperfections. A foundation is typically applied under other colored cosmetics and provides a uniform layer of color and skin coverage which improves the overall appearance of make-up.

Several characteristics are important for a cosmetic foundation. A foundation should have an acceptable "look" or appearance during application and after extended wear. A foundation should have a pleasant "feel" during and after application to the skin. A foundation should not produce a tacky sensation during application. In addition, a foundation should resist water, oil and abrasion and retain a "freshly applied" look.

Foundation compositions containing a film-forming polymer resin possess many of these desirable properties. For example, WO 96/33689 discloses a water-in-oil emulsion containing either the acrylic resin DERMACRYL LT from National Starch or a sulfonated polyester AQ resin available from Eastman Chemical, among other materials. When applied to the skin, these polymers are thought to form a film on the skin surface and are described as resisting cracking or peeling, and as having desirable wear properties.

SUMMARY OF THE INVENTION

Applicants have unexpectedly found that a composition containing both acrylate/acrylamide copolymers and sulfonated polyester or polyesteramide polymers provides a superior transfer-proof cosmetic.

Accordingly, one object of this invention is to provide a cosmetic composition that has improved look, feel and wear characteristics when applied to the skin.

another object is to provide a cosmetic as above that is in liquid form.

These objects and others are accomplished with a cosmetic composition, comprising:

(A) a polymer comprising repeating units resulting from the polymerization of the following monomer units:
  (1) an acrylate and/or methacrylate,
  (2) an N-substituted acrylamide, and
  (3) an unsubstituted carboxylic acid; and
(B) a polyester or polyesteramide comprising repeating units resulting from the polymerization of the following monomer units:
  (1) at least one difunctional dicarboxylic acid;
  (2) from about 4 to about 25 mole %, based on a total of all acid, hydroxyl and amino equivalents being equal to 200 mole percent, of at least one difunctional sulfomonomer containing at least one sulfonate group, where the functional groups are, independently, hydroxy, carboxyl or amino;
  (3) at least one diol or a mixture of at least one diol and at least one diamine having two —NRH groups, where R is hydrogen or a $C_1$–$C_4$ alkyl group; and
  (4) from 0 to 40 mole % of at least one difunctional reactant selected from the group consisting of hydroxycarboxylic acids having one —$C(R)_2$—OH group, aminocarboxylic acids having one —NHR group and amino-alcohols having one —$C(R)_2$—OH group and one —NHR group, where R is as defined above.

In a preferred embodiment the invention composition comprises an alkoxylated carboxylic acid surfactant, preferably of the formula:

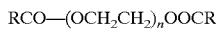

where R is a residue of a polymer of a hydroxy $C_8$–$C_{28}$ acid such as hydroxystearic acid and n is from 10–60, preferably 20–40, more preferably 25–35.

Preferably the acid is of the formula

where $y \geq 1.5x$, preferably $y \geq 2x$.

A more complete appreciation of the invention and many of the attendant advantages thereof will be readily obtained as the same becomes better understood by reference to the following detailed description.

DETAILED DESCRIPTION OF THE INVENTION

The present invention is directed to a cosmetic composition containing two polymers (A) and (B) where:

(A) is a polymer comprising repeating units derived from the polymerization of the following monomer units:
  (1) an acrylate and/or methacrylate,
  (2) an N-substituted acrylamide, and
  (3) an unsubstituted carboxylic acid; and
(B) is a sulfonated polyester or polyesteramide comprising repeating units derived from the polymerization of the following monomer units:
  (1) at least one difunctional dicarboxylic acid,
  (2) from about 4 to about 25 mole %, based on a total of all acid, hydroxyl and amino equivalents being equal to 200 mole percent, of at least one difunctional sulfomonomer containing at least one sulfonate group, where the functional groups are, independently, hydroxy, carboxyl or amino,
  (3) at least one diol or a mixture of at least one diol and at least one diamine having two —NRH groups, where R is hydrogen or a $C_1$–$C_4$ alkyl group, and
  (4) from 0 to 40 mole % of at least one difunctional reactant selected from the group consisting of hydroxycarboxylic acids having one —$C(R)_2$—OH group, aminocarboxylic acids having one —NHR group and amino-alcohols having one —$C(R)_2$—OH group and one —NHR group, where R is as defined above.

The term "cosmetic composition" is defined herein as any composition that may be safely applied to the skin, scalp, hair, face, eyelashes, lips, mucous membranes and/or nails, etc. of a subject. This term does not exclude pharmaceutically active agents from the composition.

Polymer (A) is preferably a copolymer derived from the polymerization of monomers (1)–(3) described above. The monomeric starting material which provides monomer unit (1) is preferably a $C_1$–$C_{18}$, more preferably a $C_1$–$C_8$ and most preferably a $C_1$–$C_5$ alkyl acrylate or methacrylate. Mixtures may be used. These carbon number ranges include all specific carbon numbers and subranges therebetween.

Examples of suitable acrylates and methacrylates include methyl acrylate, butyl acrylate, methyl methacrylate and isobutyl methacrylate. Polymer (A) may contain more than one acrylate and/or methacrylate. Polymer (A) preferably comprises 10–75%, more preferably 30–60% and most preferably 35–50% by weight of the acrylate or methacrylate, based on the total weight of the polymer. These weight ranges include all specific values and subranges therebetween, including 15, 20, 25, 40, 45, 55, 65 and 70% by weight.

The monomeric starting material which provides monomer unit (2) is preferably a $C_1$–$C_{18}$, more preferably a $C_3$–$C_{12}$ and most preferalby a $C_4$–$C_{10}$ N-alkyl acrylamide. These carbon number ranges include all specific carbon numbers and subranges therebetween. Suitable examples of the N-substituted acrylamide include t-butylacrylamide and t-octylacrylamide. t-Octylacrylamide is particularly preferred. Polymer (a) may contain 10–70%, preferably 15–60%, more preferably 20–40% and most preferably 25–35% by weight of the N-substituted acrylamide, based on the total weight of the polymer. These weight ranges include all specific values and subranges therebetween, including 30, 45, 50, 55 and 65% by weight.

The monomeric starting material which provides monomer unit (3) is preferably a $C_3$–$C_6$, more preferably $C_3$–$C_5$ and most preferably a $C_3$–$C_4$ unsaturated carboxylic acid. Acrylic acid or methacrylic acid is most particularly preferred. Polymer (A) preferably contains 5–40%, more preferably 5–30% and most preferably 10–15% by weight of the unsaturated carboxylic acid, based on the total weight of the polymer. These weight ranges include all specific values and subranges therebetween, including 15, 20 and 35% by weight.

Polymer (A) is preferalby soluble in alcohols (such as ethanol, isopropanol and fatty alcohols). The polymer is preferably insoluble in water. Preferably, the polymer is dispersible or soluble in water or oil after neutralizing at least a portion of the carboxylic acid groups with an appropriate base. Suitable neutralizing bases include triethanolamine, 2-amino-2-methyl-1-propylamine and inorganic hydroxides for water systems, and long chain amines for oil systems. The amount of base required can be determined by methods well-known to those of ordinary skill in the art.

Preferred examples of polymer (A) and methods of preparing the polymer are described in U.S. Pat. No. 5,288,493 and the DERMACRYL LT product brochure, National Starch and Chemical Co., 1994, both incorporated herein by reference. A particularly preferred and commercially available source of (A) is DERMACRYL LT copolymer from National Starch and Chemical Co., Bridgewater, N.J., USA.

The composition may contain up to 12% by weight of polymer (A), based on the total weight of the composition. Preferably, the composition contains 0.05 to 12%, more preferably, 0.5 to 8%, even more preferably 0.75 to 5% and most preferably 0.9 to 3% by weight of (A), based on the total weight of the composition. These ranges include all specific values and subranges therebetween, including 0.1, 0.2, 1, 2, 4, 6, 7, 9, 10 and 11% by weight.

Polymer (B) is a sulfonated polyester or polyesteramide having ester or ester and amide repeating units derived from the polymerization of monomers (1)–(4) described above.

Difunctional dicarboxylic acid component (1) may comprise an alkyl dicarboxylic acid, an aromatic dicarboxylic acid or a mixture thereof. Preferably, the difunctional dicarboxylic acid does not contain any functional groups other than the carboxylic acid groups. Preferably, dicarboxylic acid component (1) comprises a $C_2$–$C_{10}$ alkyl dicarboxylic acid, a $C_6$–$C_{12}$ aromatic dicarboxylic acid or a mixture thereof. More preferably, dicarboxylic acid component (1) comprises a $C_2$–$C_{10}$ linear alkyl dicarboxylic acid, a $C_2$–$C_8$ cyclic alkyl dicarboxylic acid, a $C_6$–$C_{10}$ aromatic dicarboxylic acid or a mixture thereof. These ranges include all specific values and subranges therebetween. Most preferably, the dicarboxylic acid component comprises a phenyl dicarboxylic acid. Suitable dicarboxylic acids include succinic, glutaric, adipic, azelaic, sebacic, itaconic, 1,4-cyclohexanedicarboxylic, phthalic, terephthalic and isophthalic acid. Other suitable acids are disclosed in U.S. Pat. No. 3,779,993, incorporated herein by reference. Isophthalic acid is particularly preferred. If terephthalic acid is used as the carboxylic acid component of the polymer, superior results are achieved when at least 5 mole percent of one or the other acids is also used. The term "dicarboxylic acid" and "carboxylic acid" as used herein includes the corresponding activated acid equivalents, including anhydrides, esters and acid halides (such as acid chlorides).

The difunctional sulfomonmer component (2) is always different from component (1) and may be a dicarboxylic acid or ester thereof containing a sulfonate group, a glycol containing a sulfonate group or a hydroxyacid containing a sulfonate group. Mixtures of these monomers may be used. Difunctional sulfomonomer component (2) preferably comprises an alkyl dicarboxylic acid or an aromatic dicarboxylic acid containing a sulfonate group, or a mixture thereof. More preferably, component (2) comprises a sulfonated $C_2$–$C_{10}$ alkyl dicarboxylic acid or a $C_6$–$C_{12}$ sulfonated aromatic dicarboxylic acid. These carbon number ranges include all specific values and subranges therebetween. Suitable aromatic groups in these sulfonated dicarboxylic acids include phenyl, naphthyl, diphenyl, oxydiphenyl and methylenediphenyl groups. Most preferably, component (2) comprises a sulfonated phenyl dicarboxylic acid. Suitable sulfonated dicarboxylic acids include sulfophthalic acid, sulfoterephthalic acid, sulfoisophthalic acid and 4-sulfonaphthalene-2,7-dicarboxylic acid. 5-Sulfoisophthalic acid is particularly preferred.

The sulfonate group ($-SO_3^-$) is preferably a salt of a suitable cation. Suitable cations include monovalent cations (such as $Na^+$, $Li^+$, $K^+$, $NH_3^+$), divalent cations and trivalent cations. Metal ions are preferred cations. Monovalent metal ions are more preferred. Sodium is a particulary preferred cation. The cation may be exchanged using ion exchange techniques well-known to those of ordinary skill in the art. The choice of cation for the sulfonate group may affect the dispersibility of the polymer as described in column 4 of U.S. Pat. No. 4,946,932, incorporated herein by reference.

The molar ratio of difunctional dicarboxylic acid component (1) to sulfonated dicarboxylic acid component (2) may be 1.85 to 19, preferably 2.3 to 19, more preferably 2.3 to 9 and most preferably 3 to 5.7. These ranges include all specific ranges and subranges therebetween, including 2, 2.5, 3.5, 4, 4.5, 5, 5.5, 6, 7, 8, 9 and 10.

When the sulfonate-containing difunctional monomer is a carboxylic acid or equivalent thereof, the polymer preferably contains at least 8 mole %, more preferably at least 10 mole % of this monomer based on the total acid content. The total acid content is defined as the sum of (a) moles of difunctional dicarboxylic acid component (1), (b) moles of component (2) which are dicarboxylic acids, (c) one-half of the moles of component (2) which are monocarboxy-containing compounds and (d) one-half of the moles of component (4).

Component (3) may contain at least one diol or a mixture of a at least one diol and at least one diamine. The diol preferably contains two —CH$_2$—OH groups. Component (3) preferably comprises at least one diol. Preferably, component (3) comprises a polyethylene glycol, an alkyl diol, an aralkyl diol or a mixture thereof. More preferably, the diol component comprises a polyethylene glycol having the formula H—(OCH$_2$CH$_2$)$_n$—OH, where n is any integer from 2 to 500, a C$_2$–C$_{12}$ alkyl diol, a C$_6$–C$_{10}$ aralkyl diol or a mixture thereof. Suitable poly(ethylene glycols) include relatively high molecular weight polyethylene glycols available commercially under the designation CARBOWAX from Union Carbide. Suitable alkyl and aralkyl diols include ethylene glycol, propylene glycol, 1,3-propanediol, 2,4-dimethyl-2-ethylhexane 1,3-diol, 2,2-dimethyl-1,3-propanediol, 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-trimethyl- 1,6-hexanediol, thiodiethanol, 1,2-cyclohexanedimethanol, 1,3-cyclohexanedimethanol, 1,4-cyclohexanedimethanol, 2,2,4,4-tetramethyl-1,3-cyclobutanediol and p-xylylenediol.

Most preferably, the diol component comprises ethylene glycol, diethylene glycol, 1,4-cyclohexanedimethanol or mixtures thereof. A mixture of diethylene glycol and 1,4-cyclohexanedimethanol is particularly preferred. Preferably, this mixture contains 40–85 mole % diethylene glycol and 15–60 mole % 1,4-cyclohexanedimethanol, more preferably 45–65 mole % diethylene glycol and 35–60 mole % 1,4-cyclohexanedimethanol and most preferably 45–60 mole % diethylene glycol and 40–55 mole % 1,4-cyclohexanedimethanol. These ranges include all specific values and subranges therebetween.

Polymer (B) may contain up to 40 mole % of component (4). Preferably, (B) contains 0 to 25 mole % and more preferably 0 to 10 mole % of component (4). Most preferably, (B) does not contain any repeating units derived from the monomers of component (4).

Up to 80% of the linking groups in polymer (B) may be amide groups. Preferably, 0 to 40%, more preferably 0 to 20 and most preferably 0 to 10% of the linking groups in (B) are amides. In a particularly preferred embodiment, (B) is a polyester containing repeating units resulting from the polymerization of (1) at least one difunctional dicarboxylic acid, (2) at least one sulfonated dicarboxylic acid and (3) at least one diol. The preferred embodiments for monomers (1)–(3) are discussed above.

Polymer (B) preferably has an inherent viscosity of 0.1 to 1.0, preferably 0.15 to 0.6, more preferably 0.2 to 0.6 and most preferably 0.25 to 0.5. These viscosity ranges include all specific ranges and subranges therebetween. The inherent viscosity is preferably measured according to ASTM D2857-70 procedure as described in columns 7 and 8 of U.S. Pat. No. 5,260,052, incorporated herein by reference.

The molecular weight, $M_n$, of Polymer (B) is preferably 1,800–3,500, more preferably 1,800–3,000, and most preferably 2,000–2,500, when measured by gel permeation chromatography (GPC) using a polystyrene standard. Using a polyester standard, $M_n$ is preferably 12,500–15,500, more preferably 13,000–15,000 and most preferably 13,500–14,500. These $T_g$ ranges for $M_n$ include all specific values and subranges therebetween.

Polymer (B) may have a $T_g$ of 27–65° C., preferably 30–65° C., more preferably, 45–60° C. and most preferably 50–60° C. These ranges include all specific values and subranges therebetween.

Preferably, each molecule of polymer (B) contains 5 to 8 sulfonated dicarboxyl groups. Preferably, each polymer molecule is linear in structure, i.e., the polymer is not crosslinked. The polymer is preferably dispersible in water without the aid of a surfactant. The polymer is preferably synthesized by melt-phase condensation of the monomeric components. Preferred examples of polymer (B) are described in U.S. Pat. Nos. 3,546,008, 3,734,874, 3,779,993, 4,233,196, 4,335,220, 4,946,932, 5,260,052, 5,266,322, 5,314,684 and in the AQ 55S and AQ 38S product brochure, Eastman Chemical Co., 1994, all of which are hereby incorporated by reference. A particularly preferred and commercially available source of polymer (B) is AQ 55S, AQ 38S and AQ 29 polymers from Eastman Chemical Co., Kingsport, Tenn., USA. Typical repeating units of these polymers are disclosed in column 7 of U.S. Pat. No. 5,260,052, incorporated herein by reference. The AQ 55S polymer is particularly preferred.

The composition may contain up to 12% by weight of (B), based on the total weight of the composition. Preferably, the composition contains 0.05 to 12%, more preferably 0.5 to 8%, even more preferably 0.75 to 5% and most preferably 0.9 to 3% by weight of polymer (B). These weight % ranges include all specific values and subranges therebetween, including 0.1, 0.2, 0.3, 0.4, 1.0, 2.0, 4.0, 6.0, 7.0, 9.0, 10 and 11% by weight.

In a preferred embodiment, the composition contains synergistic amounts of polymers (A) and (B). The term "synergistic amounts" is defined as weight amounts of each polymer (A) and (B) that provide greater-than-additive performance with regard to transfer resistance than the same total weight of polymer (A) or polymer (B) alone. In other words, the synergistic combination of polymer (A) and (B) provides a transfer resistant effect greater than the same weight amount of either polymer used individually.

Preferably, the combined amount of (A) and (B) in the composition is 0.1 to 12% by weight. More preferably, 1 to 8% and most preferably 2.5 to 5% by weight. These weight range includes all specific values and subranges therebetween, including 2, 4, 6, 8, and 10 wt %.

Transfer resistance is preferably measured by applying the composition to glass, allowing the composition to set at room temperature (62°–75° F.) for 75 minutes, followed by rubbing with the fingers. Transfer resistance can also be measured by applying the composition to the skin and, after allowing the composition to set, pressing and/or gently swiping the composition with a white cotton cloth.

The invention may preferably contain an alkoxylated carboxylic acid surfactant as described above in amounts of from 0.1–10% by weight based on total weight, including 0.5, 1, 1.5, 2, 2.5, 3, 3.5, 4, 4.5, 5, 5.5, 6, 6.5, 7, 7.5, 8, 8.5, 9 and 9.5 and all values and subranges therebetween. Arlacel P135 (ICI surfactants) is preferred. See page 694 of the International Cosmetic Ingredient Dictionary, Volume 1, 1995, CTFA, incorporated herein by reference. Arlacel P135 is PEG-30 dipolyhydroxystearate. This surfactant is preferably present when the invention compositions are in liquid form, meaning a form which runs at room temperature (68–75° F.) and which can wet a surface such as a cosmetic application brush. When the invention composition is in liquid form it preferably has a viscosity of 90,000–126,000 measured with an RVT spindle D at 5 rpm and 25° C.

The composition may additionally contain a water-miscible and/or water-dispersible solvent. Preferably, the solvent is a plasticizer and may also act as a humectant. The term "plasticizer" as used herein refers to a solvent that softens a synthetic polymer. This solvent preferably evaporates slowly from the surface of the skin. Suitable solvents include branched hydrocarbons such as C$_3$–C$_{24}$, preferably C$_{10}$–C$_{14}$, branched alkanes such as isododecane (CTFA), glycols, glycol ethers, carbonates and isosorbides. Preferred solvents include propylene glycol, butylene glycol, hexylene glycol, glycerine, dipropylene glycol, dipropylene glycol methyl ether, propylene glycol phenyl ether, polyethylene glycols (such as PEG 6 and PEG 8), propylene carbonate, dimethyl isosorbide and mixtures thereof. Other plasticizing solvents are disclosed in the *International Cosmetic Ingredient Handbook*, Third Edition, 1995, pp. 896–897, published by the Cosmetic, Toiletry, and Fragrance Association and WO 96/33689, both incorporated herein by reference. A particularly preferred solvent is 1,3-butylene glycol (also a humectant).

The composition may contain 0.5 to 25 wt. % of the water-miscible and/or water-dispersible solvent. Preferably the composition contains 1 to 20%, more preferably 2 to 15% and most preferably 4 to 10 by weight of this solvent. These weight % ranges include all specific values and subranges therebetween. The weight ratio of the water-miscible or water-dispersible solvent to the total amount of polymers (A) and (B) may be 0.1 to 10. More preferably, this ratio is 0.2 to 5, even more preferably 0.3 to 4 and most preferably 0.5 to 3. These ratio ranges include all specific values and subranges therebetween, including 0.75, 1, 1.5, 1.75, 2, 2.25, 2.5, 2.75, 3.5, 4.5, 6, 7, 8, and 9.

The composition may contain 20 to 80% by weight water, based on the total weight of the composition. Preferably the composition contains 20 to 70%, more preferably 25 to 60% and most preferably 30 to 50% by weight water. These weight % ranges include all specific values and subranges therebetween, including 35, 40, 45, 55, 65 and 75% by weight. The water used to formulate the present composition is preferably deionized to avoid incompatibility with polymers (A) and/or (B).

The present composition may contain only an aqueous phase, only an oil phase, or only a solid phase, including pastes. Alternatively, the composition may be an emulsion. The term "emulsion" includes an oil-in-water emulsion and a water-in-oil emulsion. Preferably, the composition is a water-in-oil emulsion. Preferably, polymers (A) and (B) are in the inner aqueous phase of a water-in-oil emulsion.

When the invention composition is an oil phase, an oil-containing paste, or an emulsion, it contains oil. The oil phase preferably contains cosmetically acceptable hydrophobic and/or lipophilic substances well-known to those or ordinary skill in the art. Preferably, the oil phase contain paraffins, hydrocarbons, esters, ethers, silicones, waxes and mixtures thereof. A highly preferred oil phase is one or a mixture of a linear or branched hydrocarbon oil such as isododecane (CTFA) or any other linear or branched alkane or alkene (preferably of $C_6$–$C_{24}$). Silicone oils are less preferred due to their compatibility with polymer (A).

Preferably, the oil phase comprises 5–40%, more preferably 10–30 percent of the total weight of the composition, including 12, 14, 16, 18, 20, 22, 24, 26 and 28 percent. These weight ranges include all specific values and subranges therebetween.

The composition may additionally contain one or more emulsifiers. The term "emulsifier" includes ionic and non-ionic emulsifiers. Emulsifiers are well-known to those of ordinary skill in the art and constitute a large group of conventional and commercially available products. Emulsifiers are characterized by their hydrophilic-lipophilic balance (HLB). HLB values are given in the literature for many common emulsifiers and, if not, may be calculated by art-known methods such as by the formula given in column 3 of U.S. Pat. No. 5,015,469, incorporated herein by reference.

Oil-in-water emulsifying agents preferably have an HLB of greater than 6.0 and produce emulsions in which water forms the continuous phase. Emulsifiers of this type include PEG 300 distearate, sorbitan monolaurate and triethanolamine stearate.

Water-in-oil emulsifiers may have an HLB of less than 6.0, preferably below 5, and produce emulsions in which the oil forms the continuous phase. Such emulsifiers include, lanolin alcohols, ethylene glycol monostearate, sorbitan mono-oleate and PEG 200 dilaurate. Emulsifiers with HLB's of between 5 and 7 may function as either oil-in-water or water-in-oil emulsifiers, depending on how they are used.

Other suitable oil and water emulsifiers (surfactants) useful in the present invention include those meeting the above HLB constraints described in U.S. Pat. No. 4,311,695 (Dow), U.S. Pat. No. 4,782,095 (Union Carbide), U.S. Pat. No. 4,698,178 (Goldschmidt), and U.S. Pat. No. 4,122,029 (Dow), all incorporated herein by reference, as well as those disclosed in McCutcheon's, *Detergents and Emulsifiers*, North American edition (1986), published by Allured Publishing Corporation, McCutcheon's *Functional Materials*, North American edition (1992), WO 96/33689, pp.11–12, and *International Cosmetic Ingredient Handbook*, Third Edition, 1995, pp. 919–925, published by the Cosmetic, Toiletry, and Fragrance Association, all incorporated herein by reference. Other non-limiting examples of suitable emulsifiers (surfactants) for use in the compositions of the present invention include those meeting the invention HLB constraints listed in the following U.S. Pat. Nos. 5,151,210, 5,151,209, 5,120,532, 5,011,681, 4,788,006, 4,741,885, 4,704,272, 4,557,853, 4,421,769, and 3,755,560, all incorporated herein by reference. Other useful surfactants include stearamine oxide, disodium stearyl sulfosuccinate, dihydroxyethyl lauramine oxide, disodium oleth-3 sulfosuccinate, behenamine oxide, hydroxydecyl maltitol and sodium octyl sulfate.

The amount of emulsifier used in the composition may vary widely. Preferably, the composition contains an emulsion-stabilizing amount of the emulsifier. More particularly, the amount of the emulsifier may vary from 0.1 to 25% by weight of the composition and preferably from about 1 to 10% by weight. These weight ranges include all specific values and subranges therebetween.

The composition may additionally contain pigments, colorants and fillers. There are no specific limitations as to the pigment, colorant or filler used in the invention composition. Each may be a body pigment, inorganic white pigment, inorganic colored pigment, pearling agent, and the like. Non-limiting examples include talc, mica, magnesium, carbonate, calcium carbonate, magnesium silicate, aluminum magnesium silicate, silica, titanium dioxide, zinc oxide, red iron oxide, yellow iron oxide, black iron oxide, ultramarine, nylon powder, polyethylene powder, methacrylate powder, polystyrene powder, silk powder, crystalline cellulose, starch, titanated mica, iron oxide titanated mica, bismuth oxychloride, etc. These pigments and powders can be used independently or in combination. Other suitable pigments, colorants and fillers are disclosed in WO 96/33689, pp. 10–11 and the *International Cosmetic Ingredient Handbook*, Third Edition, 1995, published by the Cosmetic, Toiletry, and Fragrance Association, pp. 871 and 873–875, both incorporated herein by reference.

The pigments are typically used as opacifiers and colorants. They are preferably present in a concentration sufficient to provide a pleasing color to the composition in the container in which the composition is sold and to confer the desired coverage and color to skin when applied. These pigments may be used as treated particles, or as the raw pigments themselves. Typical pigment levels are selected for the particular purpose of the composition. For example, a foundation for fair skinned individuals would typically use lighter pigments and those pigments in a lower amount, while a foundation for darker skinned individuals may require darker pigmentation and/or more pigmentation. Determination of these levels and pigment types is within the skill of the artisan.

Preferably, the pigments are surface treated to provide added stability of color and ease of formulation. Hydrophobically treated pigments (e.g., isopropyl titanium triisostearate-treated pigments, etc.) are more preferred, because they may be more easily dispersed in the oil phase.

Filler powders may be used to modify the density, feel or thickness of the compositions or as a matte finishing agent to hide skin defects and reduce shine. Non-limiting examples include spherical silica, hydrated silica, silicone-treated silica beads, mica, talc, polyethylene, bentonite, hectorite, kaolin, chalk, diatomaceous earth, attapulgite, etc. Of course, mixtures may be used. Of the components useful as a matte finishing agents, low luster pigment, talc, polyethylene, hydrated silica, kaolin, titanium dioxide, titanated mica (mica coated with titanium dioxide) and mixtures thereof are preferred.

The present composition may additionally contain one or more cosmetic and/or dermatological active agents. The term "cosmetic and/or dermatological active agent" as used herein includes any substance having a cosmetic and or dermatological effect when applied to the skin, scalp, lips, face, eyelashes, hair, mucous membranes and/or nails, etc. of a subject. Suitable cosmetic and/or dermatological agents which may be used in the present composition include antibacterial, antiparasitic, cosmetic biocide, antifungal, antiviral, anti-inflammatory, antipyretic, anesthetic, keratolytic, anti-free radical, antiseborrhoeic, antidandruff and antiacne agents. Other examples include an agent for reducing the visible signs of aging, an agent for modulating skin differentiation and/or proliferation and/or pigmentation, vitamins or derivative thereof and sunscreens. Examples of cosmetic and/or dermatological active agents are disclosed in *International Cosmetic Ingredient Handbook*, Third Edition, 1995, pp. 855–935, published by the Cosmetic, Toiletry, and Fragrance Association, incorporated herein by reference. Preferably, the cosmetic and/or dermatological active agent is compatible with the polymer (A) and (B). The composition may contain 0.05 to 10% by weight of these cosmetic and/or dermatological active agents.

The present composition may also contain adjuvants which are well-known to those of ordinary skill in the art. Preferable adjuvants are moisturizing agents, preservatives, antioxidants, complexing agents, perfumes, bacteriocides and odor absorbers. Examples of suitable adjuvants are disclosed in *International Cosmetic Ingredient Handbook*, Third Edition, 1995, pp. 855–935, published by the Cosmetic, Toiletry, and Fragrance Association, incorporated herein by reference. The amount of adjuvant in the composition may vary widely. Preferably the composition contains 0.1 to 20% by weight of these adjuvants. This range includes all specific values and subranges therebetween. The adjuvants may be present in the aqueous phase and/or the oil phase.

The present composition is prepared using procedures well-known to those of ordinary skill in the art. See, in particular, *Emulsions and Emulsion Technology*, Part I, Ed. Kenneth J. Lissant, Marcel, Decker, Inc., New York (1974), incorporated herein by reference. When the composition contains only an aqueous phase, the components are preferably mixed and stirred until homogeneous. Heat may be used if desired. When the composition additionally contains an oil phase the components of the aqueous phase and the oil phase are preferably mixed separately and then combined. The aqueous phase may be added to the oil phase. Alternatively, the oil phase may be added to the aqueous phase. After combining the two phases, the mixture is preferably mixed until homogeneous. The composition may be in the form of a lotion, cream, gel, paste, etc. It is highly preferred that the water phase be heated to 80° C. before polymer A (Dermacryl®, etc. polymers) are added and once added that the water phase be maintained at this temperature for 30 minutes before other materials are added.

The present composition may be used as a cosmetic for the skin, scalp, lips, face, eyelashes, hair, mucous membranes, and/or nails, etc. The composition is preferably used as a lipstick, eyeliner or cosmetic foundation for the skin. Here, an effective amount of the composition is applied to the desired area by the user. Preferably, the foundations are applied by rubbing with an application or the fingers.

Having generally described this invention, a further understanding can be obtained by reference to certain specific examples which are provided herein for purposes of illustration only and are not intended to be limiting unless otherwise specified.

All weight percentages herein are based on total weight of composition.

EXAMPLES

Example 1

Water-in-Oil Emulsion.

The quantities listed are approximate and are percent by weight based on total weight.

| Component | % | |
|---|---|---|
| Water | 37.00% | |
| Triethanolamine 99% | 1.00% | |
| Dermacryl LT (Polymer A) | 2.30% | |
| Eastman AQ55S Polymer (Polymer B) | 1–2% | (1.3%) |
| Liposorb L-20 | 0.50% | |
| Dipotassium Glycerrhizinate | 0.10% | |
| Bio-sodium Hyaluronate | 0.01% | |
| 1,3 Butylene Glycol | 6.00% | |
| Methylparaben, USP | 0.15% | |
| Hetester FAO | 1.00% | |
| Permethyl 102A | 2.00% | |
| Abil EME90 | 3.00% | |
| Trivent NP-13 | 2.75% | |
| Siliconyl Beeswax | 2.00% | |
| Vitamin E USP/Cosmetic Grade | 0.10% | |
| Vitamin A Palmitate | 0.10% | |
| Emulsynt 1055 | 1.00% | |
| Elefac 1-205 | 1.50% | |
| Propylparaben, USP | 0.20% | |
| Permethyl 99A | 13–15% | (13.7%) |
| Arlacel P135 | 1–1.5% | (1%) |
| Titanium Dioxide BD-401 | 8.50% | |
| Yellow Oxide BYO-201 | 1.01% | |
| Red Cxide BRO-12 | 0.24% | |
| Black BBQ-12 | 0.17% | |
| Talc BTS-CO1 | 1.23% | |
| Sillica MSS-500/3 | 1.00% | |
| UV Titan M160 | 6.00% | |
| Orgasol 2002D Natural Extra | 2.00% | |
| Germall II | 0.25% | |
| Emeressence 1150 | 0.20% | |
| Absorbant powder (optional) | 0.50% | |
| TOTAL | 100.00 | |

| Component | % | |
|---|---|---|
| Water | 41.79 | 41.79 |
| Triethanolamine 9% | 1.00 | 1.00 |
| Eastman AQ55S Polymer (Polymer B) | 2.00 | 2.00 |
| Liposorb L-20 | 0.50 | 0.50 |
| Bio-sodium Hyaluronate | 0.01 | 0.01 |
| Dipotassium Glycyrrhizinate | 0.10 | 0.10 |
| Dermacryl LT (Polymer A) | 2.30 | 2.30 |
| Vitamin E Acetate | 0.10 | 0.10 |
| Vitamin A Palmitate | 0.10 | 0.10 |
| Abil Wax EM 90 | 3.00 | 3.00 |
| Hetester FAO | 2.50 | 2.50 |
| Trivent NP-13 | 1.00 | 1.00 |
| Siliconyl Beeswax | 1.00 | 1.00 |
| Emulsynt 1055 | 1.00 | 1.00 |
| Elefac 1-205 | 1.50 | 1.50 |
| Propylparaben, USP | 0.20 | 0.20 |
| Permethyl 99A | 15.50 | 15.50 |
| Color Mix RBJ12-87C | 26.00 | — |
| Color Mix RBJ12-87D | — | 26.00 |
| Preservative | 0.60 | 0.60 |
| TOTAL | 100 | 100 |

| Component | % |
|---|---|
| Water | 37.10 |
| Sodium Hyaluronate | 0.10 |
| Liposorb L-20 | 0.50 |
| Dipotassium Glycerrhizinate | 0.10 |
| Triethanolamine 99% | 1.00 |
| Eastman AQ55S Polymer (Polymer B) | 1.30 |
| Dermacryl LT (Polymer A) | 2.30 |
| Butylene Glycol | 6.00 |
| Preservatives | 0.60 |
| Permethyl 102A | 1.00 |
| Vitamin E Acetate | 0.10 |
| Vitamin A Palmitate | 0.10 |
| Abil, EM 90 | 2.50 |
| Permethyl 99A | 18.38 |
| Hetester FAO | 2.00 |
| Trivent NP-13 | 1.75 |
| Elefac I-205 | 1.50 |
| Bentone Gel ISD | 1.00 |
| Beeswax | 1.00 |
| Emulysnt 1055 | 1.00 |
| Color Mix | 20.15 |
| Fragrance | 0.02 |
| TOTAL | 100 |

See the International Cosmetic Ingredient Dictionary, Vols. 1 and 2, 1995, CTFA, incorporated herein by reference, for various identities.

In order to determine transferability of the present invention composition as compared to compositions containing only one of polymers A and B the following formulations were prepared:

| Component | % |
|---|---|
| Water | 38.49 |
| Triethanolamine 99% | 1.0 |
| Dermacryl LT (Polymer A) | 2.30 |
| Liposorb L-20 | 0.50 |
| Dipotassium Glycerrhizinate | 0.10 |
| Bio-sodium Hyaluronate | 0.01 |
| 1,3 Butylene Glycol | 6.00 |
| Methylparaben, USP | 0.15 |
| Hetester FAQ | 2.00 |
| Permethyl 102A | 2.00 |
| Abil EME90 | 3.00 |
| Trivent NP-13 | 2.75 |
| Siliconyl Beeswax | 2.00 |
| Vitamin E USP/Cosmetic Grade | 0.10 |
| Vitamin A Palmitate | 0.10 |
| Emulsynt 1055 | 1.00 |
| Elefac 1-205 | 1.50 |
| Propylparaben, USP | 0.20 |
| Permethyl 99A | 13.70 |
| Arlacel P135 | 1.50 |
| Color Mix - Soft Beige | 21.15 |
| Germall II | 0.25 |
| Emeressence 1150 | 0.20 |
| TOTAL | 100.00 |

| Component | % |
|---|---|
| Water | 39.32 |
| Triethanolamine 99% | 1.00 |
| Eastman Aq55S Polymer | 1.30 |
| Liposorb L-20 | 0.50 |
| Dipotassium Glycerrhizinate | 0.10 |
| Bio-sodium Hyaluronate | 0.01 |
| 1,3 Butylene Glycol | 6.00 |
| Methylparaben, USP | 0.15 |
| Hetester FAO | 2.00 |
| Permethyl 102A | 2.00 |
| Abil EME90 | 3.00 |
| Trivent NP-13 | 2.75 |
| Siliconyl Beeswax | 2.00 |
| Vitamin E USP/Cosmetic Grade | 0.10 |
| Vitamin A Palmitate | 0.10 |
| Emulsynt 1055 | 1.00 |
| Elefac 1-205 | 1.50 |
| Propylparaben, USP | 0.20 |
| Permethyl 99A | 13.70 |
| Arlacel P135 | 1.50 |
| GW Color Mix - Soft Beige | 21.15 |
| Germall II | 0.25 |
| Emeressence 1150 | 0.20 |
| TOTAL | 100.00 |

These two compositions and a composition according to the present invention containing both Polymer A and Polymer B were applied to a glass plate and allowed to dry for 75 minutes. The dry compositions were then rubbed with the fingertips in an upward and downward motion to determine transferability. Both compositions containing only one of polymers A and B transferred easily to the fingertips, while the composition according to the present invention containing both polymers A and B did not.

In a second test the same three compositions described above were allowed to dry on the skin for five minutes and evaluated for transfer with a cotton cloth by pressing hard on top of the skin. The cloth was then examined for residual make-up and then gently swiped across the dried makeups three times and again examined. The results showed that the compositions described above containing only one of polymers A and B showed residual makeup on the cloth upon pressing and upon swiping, while the composition according to the present invention containing both polymers A and B showed no transfer upon pressing or swiping.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A cosmetic composition, comprising:
   0.05–12% by weight of (A) a polymer comprising repeating units resulting from the polymerization of the following monomers:
   (1) 10–75% by weight of at least one selected from the group consisting of a $C_1$–$C_8$ alkyl acrylate and methacrylate,
   (2) 10–75% by weight of at least one $C_3$–$C_{12}$ N-alkyl acrylamide, and
   (3) 5–30% by weight of at least one selected from the group consisting of a $C_3$–$C_6$ acrylic and methacrylic acid and
   0.05–12% by weight of (B) a polyester or polyesteramide comprising repeating units resulting from the polymerization of the following monomers:
   (1) isophthalic acid,
   (2) from about 4 to 25 mole %, based on a total of all acid, hydroxyl and amino equivalents being equal to 200 mole percent, of 5-sulfoisophthalic acid,
   (3) diethylene glycol and 1,4-cyclohexanedimethanol or a mixture of said diethylene glycol and 1,4-cyclohexanedimethanol and at least one diamine having two —NRH groups, where R is hydrogen of a $C_1$–$C_4$ alkyl group, and
   (4) from 0 to 40 mole % of at least one difunctional reactant selected from the group consisting of hydroxycarboxylic acids having one —C(R)$_2$—OH group, aminocarboxylic acids having one —NHR group and aminoalcohols having one —C(R)$_2$—OH group and one —NHR group, where R is as defined above; and wherein
   said composition further comprises an alkoxylated carboxylic acid surfactant having the formula:

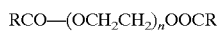
   $$RCO-(OCH_2CH_2)_n OOCR$$

wherein R is a residue of a polymer of a hydroxy $C_8$–$C_{28}$ acid and n is from 10–60.

2. The composition of claim 1, wherein the combined amount of (A) and (B) is 12% by weight.

3. The composition of claim 1, wherein the ratio of (A) to (B) is 0.1 to 10.

4. The composition of claim 5, wherein the ratio of (A) to (B) is 0.1 to 10.

5. The composition of claim 1, further comprising:
   (c) a water-miscible or water-dispersible solvent.

6. The composition of claim 5, comprising 0.5 to 25% by weight of said solvent.

7. The composition of claim 5, wherein said solvent is selected from the group consisting of glycols, glycol ethers, carbonates, isosorbides and mixtures thereof.

8. The composition of claim 1, further comprising:
   (e) water.

9. The composition of claim 8, comprising 20–80% by weight of water.

10. The composition of claim 1, further comprising:
    (e) an oil.

11. The composition of claim 10 which is a water-in-oil emulsion.

12. A method for reducing the transfer of a cosmetic composition from the wearer to another surface or person, comprising applying the cosmetic composition of claim 1 to the skin.

13. The composition of claim 1, comprising 0.9 to 3% by weight of (A) and 0.9 to 3% by weight of (B).

14. The composition of claim 1, wherein the monomer (1) in polymer (A) is selected from the group consisting of a $C_1$–$C_5$ alkyl acrylate and methacrylate.

15. The composition of claim 1, wherein the monomer (1) in polymer (A) is selected from the group consisting of methyl acrylate, butyl acrylate, methyl methacrylate, and isobutyl methacrylate and mixtures thereof.

16. The composition of claim 1, wherein polymer (A) comprises 30–60% by weight of the monomer (1).

17. The composition of claim 1, wherein the polymer (A) comprises 35–50% by weight of the monomer (1).

18. The composition of claim 1, wherein monomer (2) in polymer (A) is a $C_4$–$C_{10}$ N-alkyl acrylamide.

19. The composition of claim 1, wherein the monomer (2) in polymer (A) is a $C_3$–$C_{12}$ N-alkyl acrylamide selected from the group consisting of t-butyl acrylamide and t-octylacrylamide.

20. The composition of claim 1, wherein the polymer (A) comprises 10–70% of the monomer (2).

21. The composition of claim 1, wherein polymer (A) comprises 15–60% of the monomer (2).

22. The composition of claim 1, wherein the monomer (3) in polymer (A) is selected from the group consisting of a $C_3$–$C_5$ acrylic and methacrylic acid.

23. The composition of claim 1, wherein polymer (A) comprises 10–20% by weight of the monomer (3).

24. The composition of claim 1, wherein the polymer (A) comprises 10–15% by weight of the monomer (3).

25. The composition of claim 1, comprising 0.5–8% by weight of polymer (A).

26. The composition of claim 1, comprising 0.75–5% by weight of polymer (A).

27. The composition of claim 1, comprising 0.9–3% by weight of polymer (A).

28. The composition of claim 1, wherein monomer (3) in polymer (B) comprises 40–85 mole % diethylene glycol.

29. The composition of claim 1, wherein the monomer (3) in polymer (B) comprises 15–60 mole % 1,4-cyclohexanedimethanol.

30. The composition of claim 1, wherein the monomer (3) in polymer (B) comprises 45–65 mole % diethylene glycol.

31. The composition of claim 1, wherein the monomer (3) in polymer (B) comprises 35–60 mole % 1,4-cyclohexanedimethanol.

32. The composition of claim 1, wherein polymer (B) comprises 0–25 mole % of monomer (4).

33. The composition of claim 1, wherein polymer (B) comprises 0–10 mole % of monomer (4).

34. The composition of claim 1, wherein polymer (B) does not contain monomer (4).

35. The composition of claim 1, which comprises 0.5–8% by weight of polymer (B).

36. The composition of claim 1, which comprises 0.75–5% by weight of polymer (B).

37. The composition of claim 1, which comprises 0.9–3% by weight of polymer (B).

38. The composition of claim 1, wherein the R in said alkoxylated carboxylic acid surfactant is a residue of a polymer of hydroxy stearic acid.

39. The composition of claim 1, wherein the n in the formula for said alkoxylated carboxylic acid surfactant is from 20–40.

40. The composition of claim 1, wherein the n in the formula for said alkoxylated carboxylic acid surfactant is from 25–35.

41. The composition of claim 1, wherein said hydroxy $C_8$–$C_{28}$ acid has the formula:

$$CH_3(CH_2)_xCHOH(CH_2)_yCOOH$$

wherein $y \geq 1.5x$.

42. The composition of claim 41 wherein $y \geq 2x$.

43. The composition of claim 1, which is in the form of a liquid.

* * * * *

UNITED STATES PATENT AND TRADEMARK OFFICE
CERTIFICATE OF CORRECTION

PATENT NO. : 6,139,827

DATED : October 31, 2000

INVENTOR(S): Kenneth COHEN et al

It is certified that an error appears in the above-identified patent and that said Letters Patent is hereby corrected as shown below:

Column 13, line 46, Claim 4, "of claim 5," should read --of claim 1,--.

Signed and Sealed this

Eighth Day of May, 2001

Attest:

NICHOLAS P. GODICI

Attesting Officer

Acting Director of the United States Patent and Trademark Office